(12) United States Patent
Vanderver et al.

(10) Patent No.: US 7,691,640 B2
(45) Date of Patent: Apr. 6, 2010

(54) BIOCHEMICAL MARKER FOR DIAGNOSING A LEUKODYSTROPHY

(76) Inventors: Adeline Vanderver, 7301 Delfield St., Chevy Chase, MD (US) 20815; Yetrib Mathout, 8510 16th St., NW., Apt. 504, Silver Spring, MD (US) 20910

(*) Notice: Subject to any disclaimer, the term of this patent is extended or adjusted under 35 U.S.C. 154(b) by 955 days.

(21) Appl. No.: 11/239,256

(22) Filed: Sep. 30, 2005

(65) Prior Publication Data

US 2007/0077659 A1  Apr. 5, 2007

(51) Int. Cl.
  *G01N 33/00* (2006.01)
(52) U.S. Cl. .................. 436/86; 436/161; 436/811
(58) Field of Classification Search .............. 436/86, 436/161, 811
See application file for complete search history.

(56) References Cited

U.S. PATENT DOCUMENTS

| 5,352,616 | A | * | 10/1994 | Sundrehagen | ............... | 436/501 |
| 6,296,752 | B1 | * | 10/2001 | McBride et al. | ............ | 204/547 |
| 2002/0072596 | A1 | * | 6/2002 | Ruben et al. | ............... | 536/23.5 |
| 2003/0087450 | A1 | * | 5/2003 | Sundrehagen et al. | ......... | 436/87 |

OTHER PUBLICATIONS

Vanderver et al., Decreased Asialotransferrin in Cerebrospinal Fluid of Patients with Childhood-Onset Ataxia and Central Nervous System Hypomyelination/ Vanishing White Matter Disease., Sep. 9, 2005, Clinical Chemistry, vol. 51, pp. 2031-2042.*

* cited by examiner

*Primary Examiner*—Jill Warden
*Assistant Examiner*—Jonathan M Hurst
(74) *Attorney, Agent, or Firm*—Blank Rome LLP

(57) ABSTRACT

A biochemical marker for the diagnosis of a central nervous system leukodystrophic genetic disorder, e.g., Childhood Onset Ataxia and Central Nervous System Hypomyelination (CACH)/Vanishing White Matter Disease (VWM) has been discovered herein. Such a marker has been found in the cerebrospinal fluid (CSF) of such patients. A two dimensional gel electrophoresis/mass spectrometry or image analysis of stained transferrin isoforms approach revealed that patients with CACH/VWM have a pronounced deficiency of the basic asialo form of the transferrin compared to the amounts of asialotransferrin normally present in CSF from healthy controls or other CNS disorders. The acidic sialotransferrin isoform is not reduced in these disorders. The transferrin isoform abnormality described in the CSF of patients with CACH/VWM is unique and may be used as a clinical diagnostic biomarker. The rapid (48 hr) and efficient diagnosis of this disorder described herein will have great clinical utility.

5 Claims, 6 Drawing Sheets

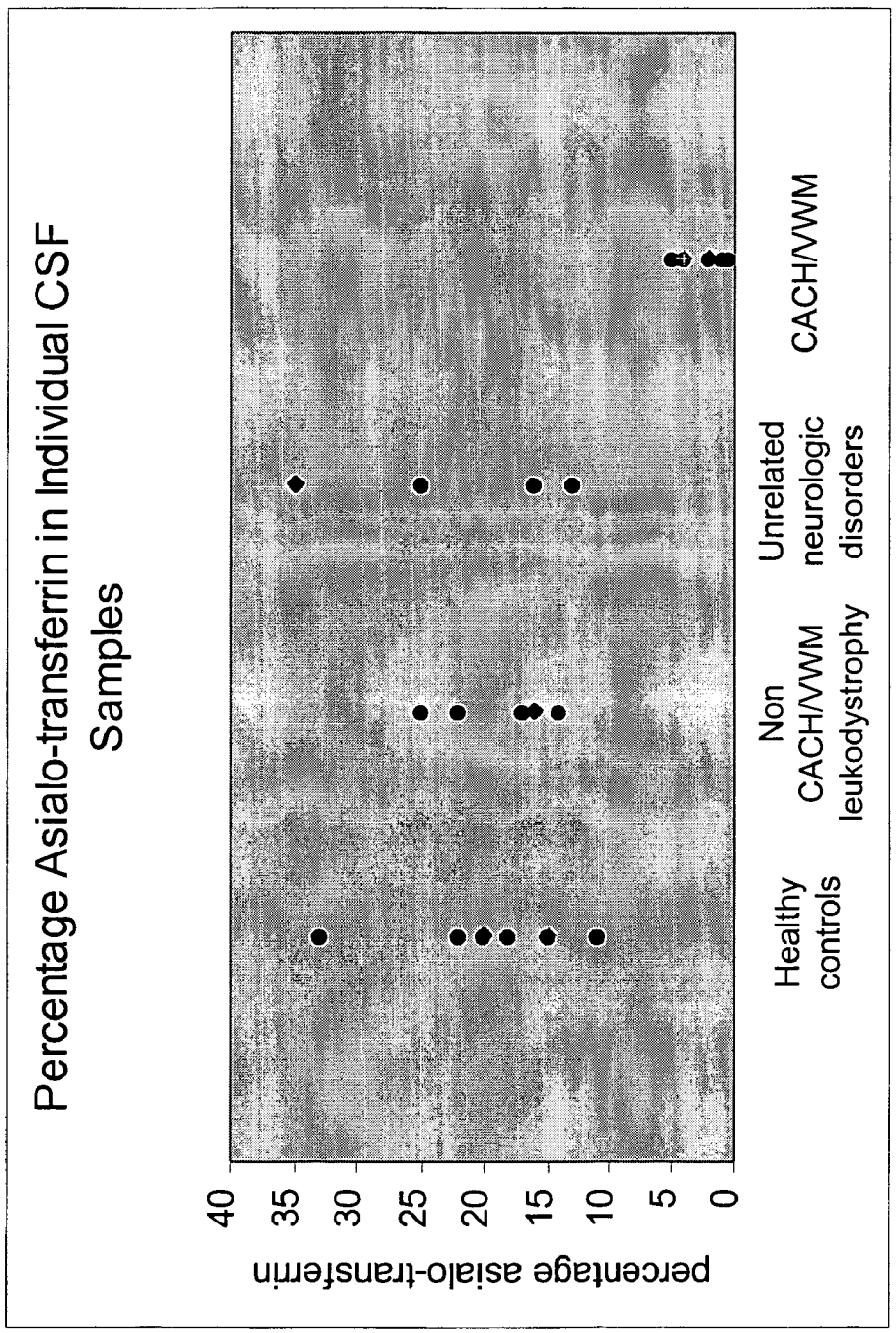

BIOCHEMICAL MARKER FOR DIAGNOSING A LEUKODYSTROPHY

This work was supported in part by a Children's Health Research Center, NIH-supported K12HD001399, by grants from the NIH (HD-P30-40677 Child Health Research Career Development Award; 1P30HD40677-01 Mental Retardation and Developmental Disabilities Research Center). Hence, the United States Government may have an interest in this invention.

FIELD OF THE INVENTION

The field of the invention is generally the use of proteomics to discover biochemical markers for central nervous diseases in patients, and to use these markers to develop diagnostic tests. More specifically, such markers were sought in leukodystrophies.

BACKGROUND

The diagnosis of unclassified leukodystrophies remains a challenge for the clinical neurologist. The leukodystrophy Childhood Onset Ataxia and Central Hypomyelination (CACH), also known as Vanishing White Matter Disease (VWM), both hereinafter referred to as CACH/VWM, is a fatal brain disorder caused by mutations in any one of the five subunits of the eukaryotic initiation factor 2B (eIF2B) (van der Knaap, MS et al, *Ann Neurol* 2002, 1, 264). This initiation factor is essential for protein synthesis and regulates translation in response to cellular stresses. CACH/VWM is though to be one of the most frequent etiologies of undiagnosed leukodystrophy.

Its diagnosis currently requires the recognition of frequently variable clinical features, magnetic resonance imaging findings that are not always specific for the disease, and sequencing of the 57 exons of the eIF2B genes associated with the disease (Leegwater. PA et al. *Nat Genet* 2001; 29:383); Schiffmann, R, et al. *Gene Reviews*. 2003-2005, www.genetests.org). This may delay or prevent accurate diagnosis in many cases.

A report has proposed elevation of cerebrospinal fluid (CSF) glycine as a biomarker for the VWM leukoencephalopathy (van der Knaap, MS et al., *J Child Neurol* 1999; 14:728). As stated by the authors, the elevations in glycine were moderate at most, and not present in all VWM patients. Most importantly, elevations in CSF glycine are observed in other neurodegenerative disorders, and thus are not specific for CACH/VWM. Do you want me to add the other references here?

CSF is a relatively accessible patient tissue, which has historically been used to investigate neurologic disorders of infectious, inflammatory, neoplastic and degenerative etiology. To a certain degree, CSF is shielded from non-neurologic protein sources by the blood-cerebrospinal fluid barrier and has a relatively slow protein turn-over. Its close contact with the brain's extracellular space makes it a very attractive source to search for biomarkers associated with neurologic disorders.

As a result of the development of effective approaches for proteome analysis, an increasing number of candidate biomarkers have been recently identified in the CSF of patients with neurologic disorders, including amyotrophic lateral sclerosis (Ramstrom M etal. *Proteomics* 2004;4:4010), multiple sclerosis (Dumont D et al., *Proteomics* 2004;4:2117), Creutzfeld Jacob disease (Sanchez JC et al. *Proteomics* 2004; 4:2229), and adult degenerative disorders such as Alzheimer's disease (Zhang J et al. *J Alzheimers Dis.* 2005;7:125). Most of these studies used either the conventional two dimensional gel electrophoresis (2-DG)/mass spectrometry (MS) approach, or shotgun proteomic approaches in combination with clustering analyses (Aebersold R et al., *Nature* 2003; 422:198). Thus, proteomics is emerging as a reliable tool to screen for disease associated biomarkers (Domon B, et al. *J Proteome Res* 2004;3:253; Marko-Varga G, et al. *J Proteome Res* 2004;3:167), but as yet has had only limited application to pediatric degenerative central nervous system disorders such as CACH/VWM.

A rapid, clinically available diagnostic test for this disorder is, therefore, highly desirable and, before this, unknown. We have discovered such a biochemical marker and have devised a diagnostic test for it in CSF that is rapid (48 hrs.) and produces unequivocal results.

SUMMARY OF THE INVENTION

We have discovered a method for diagnosing a central nervous disease (CNS) leukodystrophy in patients, comprising the steps of separating transferrin isoforms in a CSF sample taken from a patient and from control subjects, identifying the separated transferrin isoforms, then separately quantifying the separated sialo-transferrin and asialo transferrin isoforms, wherein a marked diminution of asialotransferrin, but not of sialotransferrin, relative to controls, is diagnostic for said leukodystrophy.

In one embodiment of the invention, the leukodystrophy is Childhood Onset Ataxia and CNS Hypomyelination (CACH) or Vanishing White Matter Disease (VWM).

In another embodiment, separation of the transferrin isoforms is carried out by 2-dimensional gel chromatography.

In another embodiment the separated transferrin isoforms are quantified by staining said isoforms, then—carrying out by image analysis the mass and density of each stained isoform (sialotransferrin and asialotransferrin).

In still another embodiment, the separated transferrin isoforms are quantified by staining transferrin isoform spots with a nanospray, then quantifying the mass of each isoform by mass spectrometry.

FIGURES

FIG. 1 shows representative 2-DG of the CSF proteome in controls and patients with CACH/VWM. A total of 100 μg of total protein for each sample was used for 2-DG analysis. Gels were stained with Biosafe Coumassie and scanned as described in Methods. Enlarged portions represent transferrin spots.

FIG. 2 shows portions of 2-DG of CSF proteome showing the transferrin spot pattern, in some of the controls (n=12) versus patients with CACH/VWM (n=7). There is a deficiency in basic spots in patients relative to controls. Numbers represent ratios of sialo to asialo-transferrin isoforms using 2-DG image analysis software.

FIG. 3 shows MALDI-TOF mass spectra of acidic and basic transferrin isoforms before (upper panel) and after (lower panel) treatment with neuraminidase. Analyses were performed on ABI4700 TOF-TOF Instrument operated in positive linear mode. Alpha-cyano-hydroxycinnamic acid was used as a matrix. Each spectrum represents an average of 1000 shots.

FIG. 6 shows a scatter plot of the percentage of asialotransferrin in individual CSF samples from patients and control subjects.

DETAILED DESCRIPTION OF THE METHODS USED AND PREFERRED EMBODIMENTS

Figure 1:
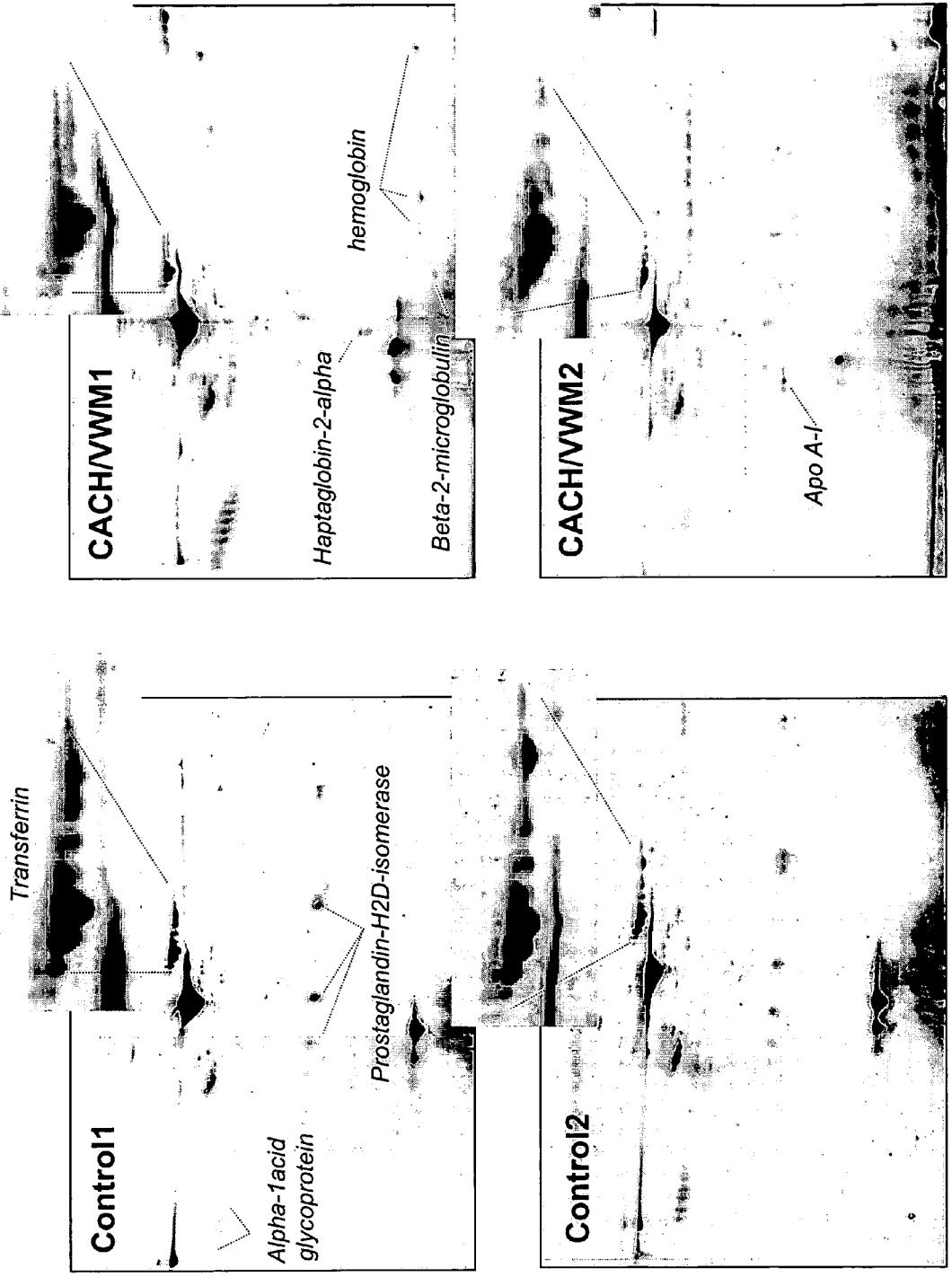

In the present study, a two-dimensional gel electrophoresis/mass spectrophotometric (2DG/MS)-based approach was used to explore possible differences between the CSF proteomes of leukodystrophic CACH/VWM patients and controls who comprised subjects undergoing lumbar puncture for medical reasons other than degenerative and/or genetic brain disorders, and patients with unrelated neurologic disorders. We hypothesized that the technique would identify a differential protein pattern between patients affected by CACH/VWM and controls. This differential protein pattern has been discovered.

We have discovered a biochemical marker for the childhood genetic disease CACH/VWM in CSF of such patients. The marker consists of a very sharp reduction (to vanishingly small amounts) of asialotransferrin, but not sialotransferrin, in the CSF of CACH/VWM patients, compared to amounts of this asialotransferrin protein present in the CSF of healthy or non-CACH/VWM neurologic patients children. This reduction provides the basis of a rapid (48 hr) diagnostic test for the disease that avoids the lengthy gene sequencing currently used for this diagnosis.

The following sections will: describe in detail how this discovery was made; provide details of a diagnostic method; and, provide quantitative data on the reduction of asialotransferrin in CSF in this leukodystrophy.

Methods

Sample Collection

All CSF samples were collected in accordance with an Institutional Review Board approved protocol at Children's National Medical Center and the collaborating institutions. Affected and disease control samples were obtained at the National Institute of Neurological Disorders and Stroke (NINDS)/ National Institutes of Health (NIH). Other control samples were obtained at Children's National Medical Center. Only excess cerebrospinal fluid drawn for other clinical or research purposes was used for these analyses.

Confirmation of eIF2B mutation status was performed at Children's National Medical Center. In total, samples from 7 patients with mutation-proven VWM and from 11 neurologically normal children with other medical reasons for lumbar puncture, and 12 with unrelated neurologic disorders (spinal muscular atrophy, white matter abnormality related to a chromosomal abnormality, Alexander disease, primary brain tumor, X-linked adrenoleukodystrophy, cervical cord lesion), were collected in sterile polypropylene cryogenic vials. Immediately after collection, each CSF sample was checked for blood contamination in a clinical lab by microscopy (assessing a standard cell count of red and white blood cells per visualized field). The CSF samples were then centrifuged at 300×g for 10 min to remove any debris. The supernatants were transferred to polypropylene tubes and stored at −80° C. until analysis.

Two Dimensional Gel Electrophoresis

Protein concentration was measured in each CSF sample using the Bio-Rad protein assay reagent (Bio-Rad, Hercules, Calif.). Typically, CSF samples showed a protein concentration ranging from 0.16 to 0.4 mg/mL. Aliquots containing 100 μg of total protein were taken from each sample and processed for 2-DG analysis as follows. Samples were desalted against 10 mM Tris HCl pH 7 using p6 Bio-Spin columns. Each solution was then dried by centrifugation under vacuum. 180 μL of rehydration buffer (7 M urea, 2 M thiourea, 2% CHAPS buffer, 50 mmol DTT and 0.5% ampholite pH 3-10) were added to the dry sample to solubilize and denature the proteins. First dimensionel ectro-focusing was performed on IPG strips (11 cm, pH 3-10) using a Bio-Rad electrofocusing chamber (Bio-Rad, Hercules, Calif.) operated as follows: 12 hours rehydration, 250 V for 15 min, 1,000 V for 1 hours and 10,000 V for 4 hours. The second dimension SDS-PGE was performed on criterion Tris-HCl (8 to 16%) pre-cast gels (Bio-Rad, Hercules, Calif). Protein spots were visualized using Bio-Safe Coomassie stain (Bio-Rad, Hercules, Calif). The gel was then scanned on a GS800 densitometer (Bio-Rad, Hercules, Calif.) and imaged as a TIFF file. The resulting gels arrays were compared using a 2-DG image analysis software, PDQuest (Bio-Rad, Hercules, Calif.), and the volume and intensity of spots of interest were determined.

Mass Spectrometry Analysis

Protein spots were excised with the tip of a polypropylene pipette and transferred into a micro centrifuge tube containing 100 μL of deionized water. The bands were destained by 2-3 washes with 100 μL of acetonitrile/water solution (50:50, v/v). Tryptic digestion was performed as previously described (Jensen, ON et al. Methods in Molecular Biology; Link et. Eds; Humana Press, Totowa, N.J. 1999; 112:513) The peptides were extracted, dried by vacuum centrifugation, redissolved in 10 μL of 0.1% TFA, and desalted using C18 ZipTip micropipette tips (Millipore Colo., Bedford, Mass.) following the manufacturer's User Guide. The peptides were eluted from the ZipTip in 10 μL of acetonitrile/0.1% TFA (70:30, v/v). Typically, 0.3 μL of peptide solution is mixed with 0.3 μL of matrix solution (50 mmol alpha cyano4-hydroxynamicacid in acetonitrile/0.1% TFA (70:30, v/v)) and spotted on the MALDI plate. Mass spectrometry (MS) and tandem mass spectrometry (MS/TMS) analyses were performed on a 4700 ABI TOF-TOF mass spectrometer (Applied Biosystems, Foster City, Calif.) equipped with Nd:YAG 200 Hz laser. The instrument was operated with delayed extraction in reflectron positive ion mode. A mixture of standard peptides was used to externally calibrate the instrument. Protein identification was carried out using the GPS explorer software (Applied Biosystems, Framingham, Mass.). Both MS and MS/TMS data were used for protein identification. To detect intact glycopeptides with high molecular masses, the 4700 ABI instrument was operated in linear positive mode and tuned for masses ranging between 2000 and 10000 Da. Accurate mass measurements were obtained by nanospray (Wilm, M. et al. *Anal Chem* 1996; 68:1) on an Apex lll Fourier transform mass spectrometer (FTMS) (23, 24) (Bruker Daltonics, Billerica, Mass.) equipped with a 7.0 T active shielded superconducting magnet and an Apollo atmospheric pressure ionization source. The home-built heated-metal desolvation capillary was kept at 120-150° C. Each experiment was performed in positive ion mode and required loading 5-10 μl of analyte solution into a freshly pulled borosilicate needle, while a platinum wire was inserted. All data were acquired in broadband mode and processed using Bruker XMASS 6.0.1 software. Tandem (MSIMS) experiments were carried out by isolating the precursor ion of interest using correlated RF sweeps (CHEF) (de Koning, LJ et al. *Int J Mass Spectrum Ion Rev* 1997;165/166:209) followed by activation through sustained off-resonance irradiation(SORI) against an argon background to obtain collision-induced dissociation (CID).

Characterization of the Glycopeptides

Glycopeptides were tentatively characterized using Glyco-Mod tool (http://au.expasy.org/tools/glycomod) by entering the observed masses (using a mass accuracy better than 10 ppm) and selecting predicted sugars moieties.The identity of target glycopeptides was further confirmed through controlled digestion with exopeptidase and exoglycosidase. Briefly, aliquots from the in-gel digest described above were dried by vacuum centrifugation, and redissolved in 10 mM ammonium bicarbonate buffer (pH 7.4). Selected aliquots were treated with a 2-3,6,8,9-neuraminidase (Calbiochem, LaJolla, Calif.) to induce hydrolysis of sialic acid-containing peptides. The remaining aliquots were treated with carboxypeptidase Y (Roche Diagnostics, Mannheim, Germany) to verify the identity of the peptide backbone. All reactions were monitored by MALDI-TOF-TOF using linear positive mode as described above.

The examples below provide details on the development of the diagnostic test and on the test itself as used clinically, and are not intended to limit the scope of the invention.

EXAMPLE 1

Two Dimensional Gel Electrophoresis

Figure 2:
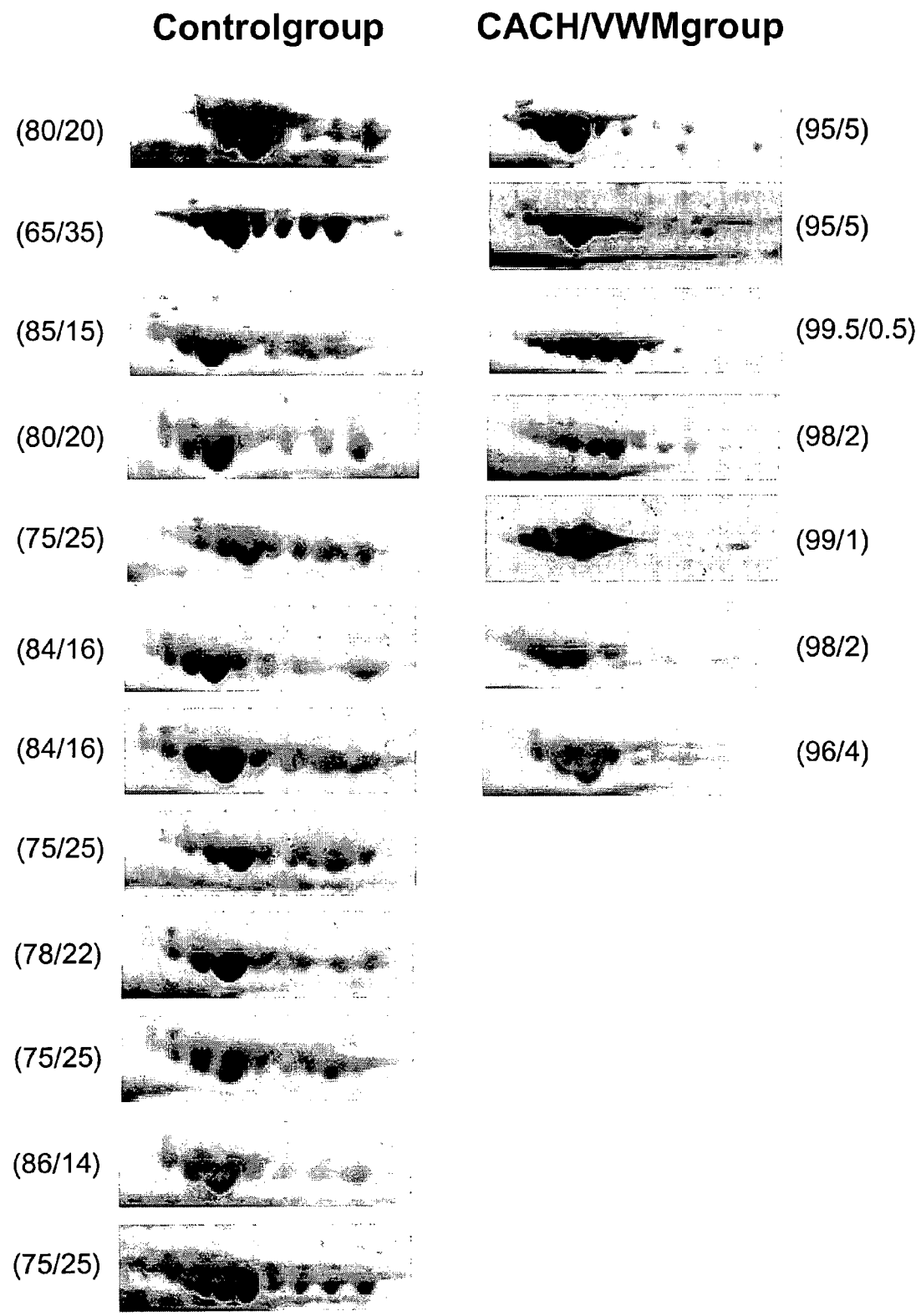

Analysis of the 2-DG spot patterns of a large number of samples (7 patients and 23 controls) led to the detection of a unique pattern in CSF of CACH/VWM patients that was not present in the controls. This pattern consisted of a variation in the composition of transferrin isoforms from CACH/VWM patients versus controls: while the latter provided 6-8 spots of transferrin with pIs ranging from 5.5 to 6.5, the former showed a greater intensity of spots with more acidic pI's (i.e., pI=5.5-6) and a lower intensity of spots with more basic pI's (pI=6-6.5) than the controls (FIG. 1). These two different patterns were reproduced among all samples from control and CACH/VWM patients respectively (FIG. 2). In all patient samples there was a great reduction in the basic transferrin spots when compared to that of controls. The number of samples analyzed was sufficient to exclude the possibility that the observed differences between 7 CACH/VWM and 23 controls were just a random event. Further, CSF samples of two additional patients suspected to have VWM were analyzed, but found to have spot patterns that were clearly closer to the controls cluster. Independent diagnosis based on gene sequencing showed that these two patients did not actually have the mutation proven for CACH/VWM. This experiment could be considered as the blinded test and show the robustness of our candidate biomarker.

EXAMPLE 2

Characterization of Gel Separated Transferrin Isoforms

Figure 3:
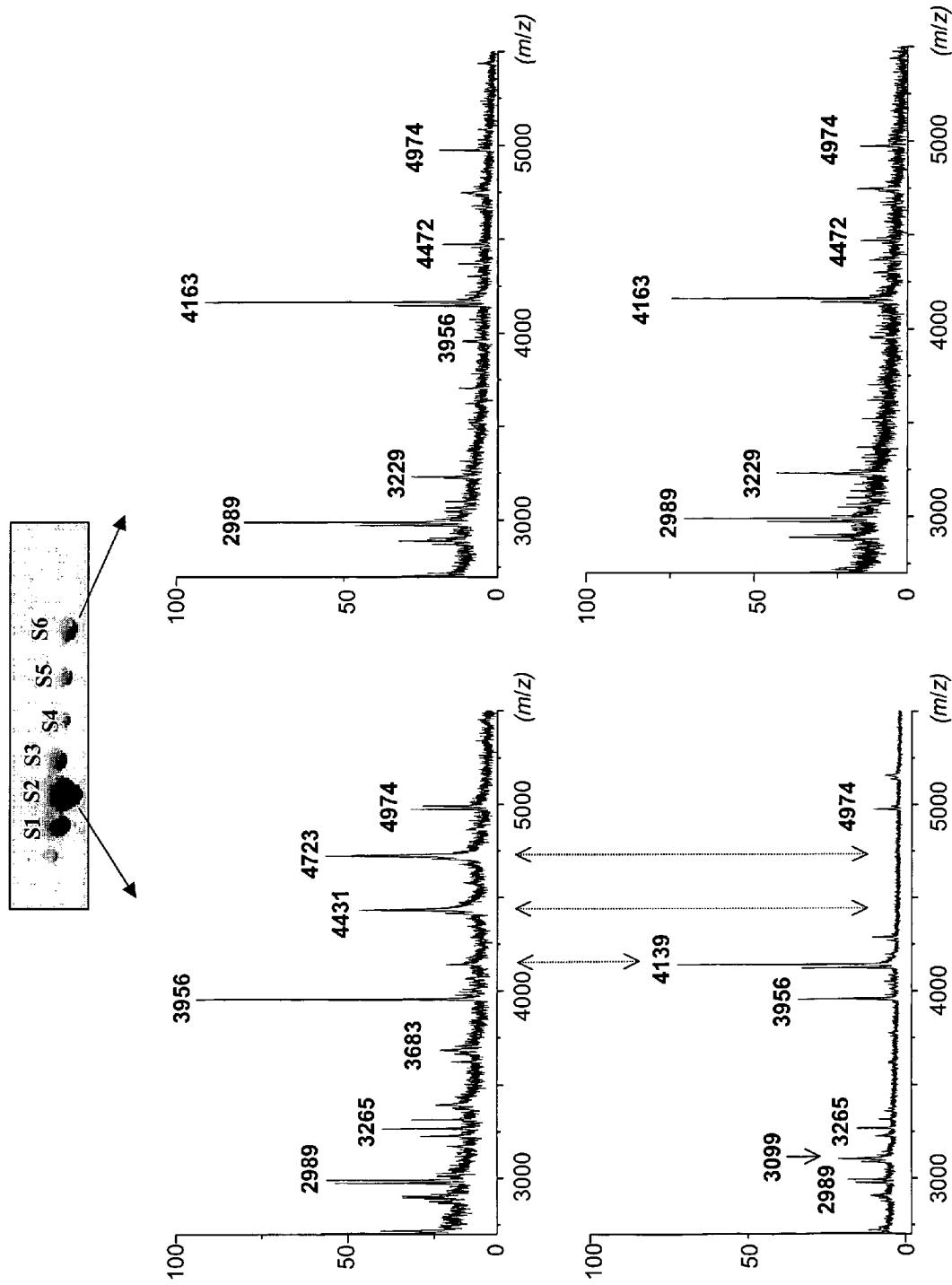

The isolated transferrin isoforms were subsequently analyzed by using a well-established mass fingerprinting strategy (Jensen, ON above). Tryptic peptides generated by in-gel digestion of the different spots were shown to cover ~69% of the protein sequence by reflectron MALDITOF-TOF analysis (Table 1; SEQ ID NOs: 1-61). However, examining the detected peptides versus the known sequence of human transferrin (Swiss-Prot accession number P02787) revealed that the maps of both acidic and basic isoforms were missing regions encompassing the known glycosylation sites (Asn432 and Asn630) (Table 1). Switching the detection mode from reflectron TOF-TOF to linear TOF afforded detection of a greater number of peaks with higher mass (FIG. 3), which we presumed could include extensive carbohydrate structures. These experiments differentiated two groups of isoforms corresponding to either the acidic spots S1, S2, S3, or to the basic S4, S5 and S6 (FIG. 3, upper panel). In particular, the acidic isoforms were characterized by signals with mass-over-charge (m/z) ratios of 4431 and 4723 that were not detected in the basic group. Contrariwise, a peak was observed at m/z 4163 for the latter set, which was not detected for the former (FIG. 3). No significant difference—was noted between S1, S2 and S3 when compared with each other, nor within the S4, S5 and S6 group. Neuraminidase treatment of the larger tryptic products resulted in the prompt elimination of the peaks at m/z 4723 and 4431, while m/z 4163 remained unaffected (FIG. 3, lower-panel). This enzymatic reaction confirmed the presence of sialic acid moieties in the acidic isoforms, which is also consistent with the IEF migration of their corresponding gel electrophoretic spots. Furthermore, the observation of a new single peak at m/z 4139, whicha accompanied the disappearances of both m/z 4723 and 4431 after neuraminidase treatment, would suggest the possible presence of either two or one sialic acid molecules in two individual glycopeptides sharing the same peptide backbone The peptide at m/z 4163 generated from the most basic transferrin spots did not seem to contain any sialic acid residue and its mass remained unchanged even after prolonged treatment with neuraminidase; this is the asialo isoform of transferrin.

EXAMPLE 3

Figure 4:
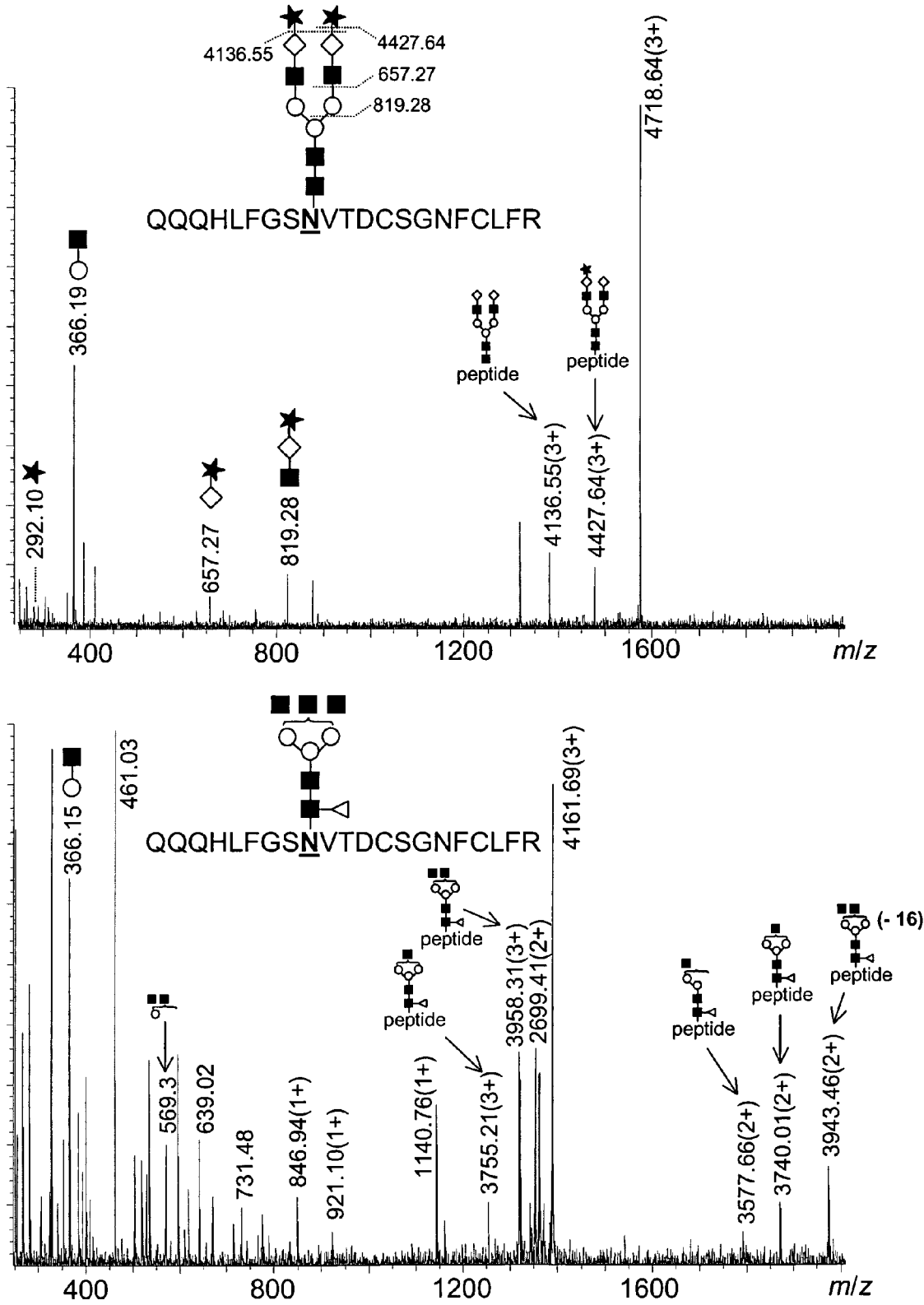
FIG. 4 shows nanospray-FTICR mass spectra of acidic (top spectrum) and basic transferring (bottom spectrum) isoforms (SEQ ID NO: 56).

Structural Characterization of the Glycopeptides Generated from Gel Separated Transferrin Isoforms Mass measurements were obtained by nanospray-FTMS analysis for each of the glycopeptides of interest (FIG. 4). Multiply charged signals were readily observed for the sialoform at m/z 1573.97 (3+), 1466.38 (4+), 1434.61 (4+), 1227.24 (3+), and 1180.72 (4+). No corresponding signals were detected for possible products generated by the asialoform(as determined by neuraminidase treatment). On the other hand, species at m/z 1388.23 (3+)and 1347.08 (2+) were observed only for the asialo-form, but not for the sialoform. The observed monoisotopic molecular masses obtained from these signals were used in GlycoMod Tool http://us.expasy.org/tools/glycomod/) to predict the putative structure of the corresponding glycopeptides (Table 2; Peptide [421-452]—SEQ ID NO: 62; Peptide [421-433]—SEQ ID NO: 38; Peptide 622-642—SEQ ID NO: 56). A mass accuracy of 10 ppm or better allowed us to minimize the incidence of possible false positive identification.

These data suggest that acidic transferrins (sialo-transferrins) are likely to include both Asn432 and Asn630 bearing the same bi-antennary carbohydrate structure composed of 2GlcNAc, 3 Man, 2 GlcNac, 2 Gal, and 2 NeuNac (see structure in Table 2). On the contrary, basic transferrins (asialo-transferrins) appear to contain a completely different form of carbohydrate side-chain attached to Asn630, corresponding to an N-linked bi-antennarystructure composed of 2GlcNAc, 3 Man, 3 GlcNac, and one Fuc (see putative structure in Table 2). It should be noted that, in agreement with our results, this particular type of glycosylation was previously described for transferrin purified from pooled human CSF samples (Hoffman, A et al. *FEBS LETT* 1995;359:164).

Close examination of tryptic digests obtained from several asialo-transferrin spots was carried out to further investigate whether the same glycosylation could be linked to theAsn432 residue, as well. While no evidence could be gathered to support this hypothesis, a peptide with monoisotopic mass of 2692.177 Da was detected in the asialo-transferrin spots, which was completely absent from the corresponding digests of sialo-transferrin spots. This peptide was only detected with ESI-FTMS and not with the MALDI-TOF/MS and its intensity was to low to confirm its exact structure. However, its mass is in close agreement with that calculated for peptide [421-433] with Asn432 modified by an asialo-carbohydrate composed of 2 GlcNAc and 5 Man (Table 2). Even though this kind of glycopeptide does occur, and it has been previously characterized in serum of patients with congenital disorders of glycosylation (Butler, M et al. *Glycobiology*2003;113:601), its occurrence in CSF asiol-transferrin is of unknown etiology.

Generally, the results provided by high-resolution nanospray-FTMS and MALDI-TOFTOFwere in excellent agreement despite the different characteristics of these ionization techniques. An exception was the detection of m/z 4431 in the MALDI spectrum of acidic-transferrin, which was not observed by nanospray analysis of the same tryptic digest. However, this signal could be produced by the loss of one sialic acid unit (−292 Da) from the peptide at m/z 4723 (corresponding to 4718.887 Da by nanospray-FTMS), which is consistent with possible in-source fragmentation processes, as previously reported for glycopeptides generated from digestion of serum transferrin (Satomi, Y et al. *FEBS LETT* 2004;576:51).

Figure 5:
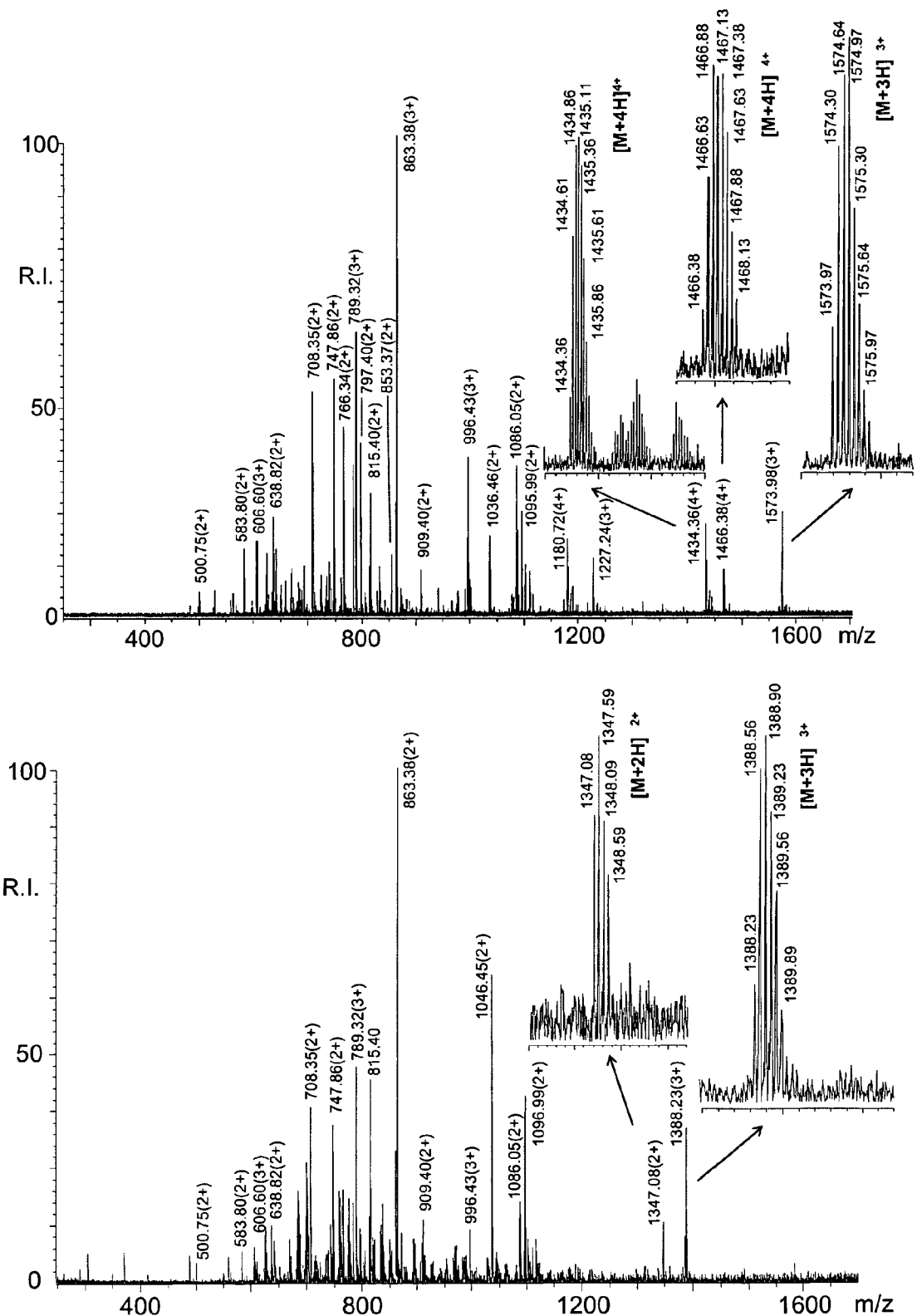
FIG. 5 shows SORI-CID analysis of sialo-glycopeptide (upper spectra) and asialo-glycopeptide (lower panel) detected in tryptic in-gel digests of transferrin spots.

Others have tested several matrix solutions for MALDI-TOF analysis of sialic acid containing peptides. It was reported that 2',4',6'-trihydroxyacetophenone (THAP) and 2,5-dihydroxybenzoic acid (DHB) offered improved detection and stability of acidic glycopeptides over alpha-cyano-4-hydroxycinnamic acid (Papac DI, et al. *Anal Chem* 1996; 68: 3215). In our hands, however, the use of DHB resulted in only a slight improvement in the stability of sialic acid containing gycopeptide. In addition, we noticed a general decrease in sensitivity for the higher m/z's, which is typical of DHB vs. CHCA. Further support for the proposed glycopeptide structures was provided by SORI-CID (see Methods) of selected precursor ions performed on the nanospray-FTMS instrument (FIG. 5 -top panel and -lower panel). Most of the fragment ions, seen in the two spectra,corresponded to cleavages occurring in the carbohydrate side chain. In general, larger fragment ions corresponded to the loss of one or two saccharide moieties from theglycopeptide while the low mass ions corresponded to fragments of the carbohydrate sidechain. In particular, the sialo-glycopeptide (4718.887 Da) produced a recognizable fragment at m/z 292 (FIG. 5 -top panel), which is indicative of the presence of sialic acid in the carbohydrate chain. On the contrary, no trace of this fragment could be observed in the spectrum of the asialo-glycopeptide (4161.730 Da, (FIG. 5 -lower panel). The very limited amounts of analyte obtained by in-gel digestion afforded CID spectra of low signal-to-noise.

Carboxypeptidase Y treatment followed by MALDI TOF-TOF analysis further confirmed the assignment of the glycopeptide with masses of 4718 Da detected in sialo-transferrin spots.The peak signal of glycopeptides with mass of 3680 and 2692 were too weak to detect their product following carboxypeptidase treatment.

While the distribution of transferrin isoforms in serum has been well characterized, due inpart to its inherent abundance and easy access, relatively little is known about transferrin isoforms in the central nervous system and CSF. Our results show that, unlike serum, normal CSF contains both sialo- and asialo-forms of transferrin. While the sialo-transferrins in our samples appear to be closely related, if not structurally identical, to those described in the serum, there are strong indications that asialo-transferrin isoforms may be brain specific. The accurate mass of glycopeptide 4161.686 Da detected in the tryptic digests of asialo-transferrin spots is consistent with a structure containing 2GlcNAc, 3 Man and 3 GlcNac, and one Fuc connected to Asn630, as reported by a group that utilized a total of 100 mL of pooled CSF samples to purify about 100 μg of asialotransferrin (Hoffman A et al. above). The same marker glycopeptide was not observed in comprehensive studies of glycosylation of serum transferrin, including patients with congenital disorders ofglycosylation who show abnormal asialo-transferrin isoforms in serum (Butler, M et al. above). Whether thissame carbohydrate is also attached to Asn432, remains to be demonstrated. A product with an accurate mass of 2692.177 Da was found with low abundance in the asialo-transferrin samples, which could possibly contain glycosylated Asn 432 (Table 2, second asialoisoform). Even though this variant of asialotransferrin glycosylation has been described in the serum of a patient with an unexplained Congenital Disorder of Glycosylation (Butler M et al., above) its occurrence in CSF asialo-transferrin still awaits further investigation.

EXAMPLE 4

Diagnostic Test for CACH/VWM in Patients

CSF samples were treated as above and subjected to the 2-DG procedure described above. Protein spots were visualized using Bio-Safe Coomassie stain (Bio-Rad, Hercules, Calif). The gel was then scanned on a GS800 densitometer (Bio-Rad, Hercules, Calif.) and imaged as a TIFF file. The resulting gels arrays were compared using a 2-DG image analysis software, PDQuest (Bio-Rad, Hercules, Calif.), and the volume and intensity of spots of interest were determined. Image analysis of the 2-DG patterns by PDquest provided a determination of the ratio of asialo- vs. sialo-transferrin in each sample. In the control samples analyzed in this study, asialo-transferrin represented 8-35% of the total CSF transferrin (mean 19.2%, 95% C.I.=16.6-21.7%), while it amounted to 0.5-5% of total transferrin (mean 2.5%, 95% C.l. =-2.2-7.2%) in CACH/VWM samples (FIG. 6). The ratio of asialo to sialo-transferrin in the control and CACH/VWM samples were statistically significantly different (t (28)=6.42, p<0.0001). When the control group was limited to the five patients with non-CACH/VWM leukodystrophies (Alexander disease, X-linked Adrenoleukodystrophy, white matter diseasewith chromosomal disorder, hypomyelination), asialo-transferrin represented 14-25% of the total CSF transferrin (FIG. 6); the ratio was still statistically significant (t(10)=8.88, p<0.0001). In agreement with the image analysis data, estimates based on the mass spectrometry analysis of tryptic digests suggested levels of asialoglycopeptide that were 8-10 times lower in patients than in controls.

As noted above, in all the control and non-CACH/VWM samples analyzed, asialo-transferrin represented 8 to 35% of total transferrin, while it only amounted to 0.5 to 5% of the total in CACH/VWM samples (see FIG. 6). This decrease in CSF asialotransferrin has, to our knowledge, not been described in any other disorders.

Seven out of seven patients with mutation proven CACH/VWM showed low to nearly undetectable amounts of asialo-transferrin in their CSF when compared to 23 unaffected controls. The CSF transferrin spot pattern demonstrated herein should serve as valuable biochemical markers for diagnosis or preliminary screening prior to gene sequencing. The presence of such biomarkers could be used to classify patients with this neurodegenerative disease.

TABLE 1

List of peptides detected in MALDI-TOF-TOF analysis of in-gel digests of human CSF transferrin spots.

| Start-End (a) | Observed (b) | Mr (calc) (b) | mass (c) | Sequence |
|---|---|---|---|---|
| 1-26 | nd | 2795.57 | | MRLAVGALLVCAVLGLCLAVPDKTVR |
| 27-37 | 1316.68 | 1316.58 | 0.10 | WCAVSEHEATK |
| 38-42 | nd | 696.30 | | CQSFR |
| 43-46 | nd | 529.23 | | DHMK |
| 47-60 | 1414.75 | 1414.71 | 0.04 | SVIPSDGPSVACVK |
| 61-61 | nd | 146.11 | | K |
| 62-69 | 996.56 | 996.47 | 0.09 | ASYLDCIR |
| 70-107 | 3953. | 3953.01 | 0.28 | AIAANV.....PVVAEFYGSK |
| 108-121 | 1628.91 | 1628.81 | 0.10 | EDPQTFYYAVAVVK |
| 122-132 | 1338.66 | 1338.63 | 0.02 | KDSGFQMNQLR Oxidation (M) |
| 123-132 | 1194.65 | 1194.55 | 0.11 | DSGFQMNQLR |
| 123-132 | 1210.63 | 1210.54 | 0.09 | DSGFQMNQLR Oxidation (M) |
| 133-143 | nd | 1199.62 | | GKKSCHTGLGR |
| 144-162 | 2170.22 | 2170.09 | 0.13 | SAGWNIPIGLLYCDLPEPR |
| 163-212 | nd | 5582.46 | | KPLEKAVA...QYFGYSGAFK |
| 213-225 | 1378.67 | 1378.69 | 0.02 | CLKDGAGDVAFVK |
| 216-225 | 977.54 | 977.48 | 0.06 | DGAGDVAFVK |
| 226-236 | 1272.71 | 1272.65 | 0.07 | HSTIFENLANK |
| 237-251 | 1881.00 | 1880. | 0.13 | ADRDQYELLCLDNTR |
| 240-251 | 1538.76 | 1538.70 | 0.05 | DQYELLCLDNTR |
| 252-273 | 2548.38 | 2548.29 | 0.10 | KPVDEYKD...VPSHTVVAR |
| 259-273 | 1688.98 | 1688.84 | 0.14 | DCHLAQVPSHTVVAR |
| 274-297 | nd | 2772.35 | | SMGGKED...QAQEHFGKDK |
| 298-310 | 1490.85 | 1490.75 | 0.10 | SKEFQLFSSPHGK |
| 300-310 | 1275.69 | 1275.62 | 0.07 | EFQLFSSPHGK |
| 311-315 | nd | 634.37 | | DLLFK |
| 316-323 | 873.46 | 873.43 | 0.02 | DSAHGFLK |
| 316-327 | 1322.75 | 1322.71 | 0.04 | DSAHGFLKVPPR |
| 328-331 | nd | 463.21 | | MDAK |
| 332-343 | 1477.80 | 1477.73 | 0.07 | MYLGYEYVTAIR |
| 332-343 | 1493.81 | 1493.72 | 0.09 | MYLGYEYVTAIR Oxidation (M) |
| 344-346 | nd | 401.24 | | NLR |

TABLE 1-continued

List of peptides detected in MALDI-TOF-TOF analysis of in-gel digests of human CSF transferrin spots.

| Start-End (a) | Observed (b) | Mr (calc) (b) | mass (c) | Sequence |
|---|---|---|---|---|
| 347-362 | 1816.90 | 1816.80 | 0.11 | EGTCPEAPTDECKPVK |
| 363-371 | 1194.55 | 1194.54 | 0.01 | WCALSHHER |
| 372-384 | 1520.82 | 1520.73 | 0.10 | LKCDEWSVNSVGK |
| 374-384 | 1279.65 | 1279.55 | 0.10 | CDEWSVNSVGK |
| 385-399 | 1724.91 | 1724.76 | 0.15 | IECVSAETTEDCIAK |
| 400-420 | 2158.13 | 2158.01 | 0.13 | IMNGEADAMSLDGGFVYIAGK |
| 421-433 | nd | 1475.74 | | CGLVPVLAENYNK |
| 434-452 | 2071.00 | 2070.92 | 0.08 | SDNCEDTPEAGYFAVAVVK |
| 453-464 | 1376.77 | 1376.69 | 0.08 | KSASDLTWDNLK |
| 454-464 | 1248.65 | 1248.60 | 0.05 | SASDLTWDNLK |
| 467-475 | 1014.54 | 1014.50 | 0.04 | KSCHTAVGR |
| 468-475 | 886.46 | 886.41 | 0.05 | SCHTAVGR |
| 476-489 | 1576.82 | 1576.81 | 0.02 | TAGWNIPMGLLYNK |
| 476-489 | 1592.80 | 1592.92 | 0.12 | TAGWNIPMGLLYNK Oxidation (M |
| 490-515 | nd | 3077.39 | | INHCRFDEFFSEGCAPGSKKKDSSLCK |
| 516-530 | 1705.92 | 1705.76 | 0.16 | LCMGSGLNLCEPNNK |
| 531-541 | 1282.64 | 1282.56 | 0.08 | EGYYGYTGAFR |
| 542-553 | nd | 1363.72 | | CLVEKGDVAFVK |
| 554-564 | 1165.63 | 1165.58 | 0.04 | HQTVPQNTGGK |
| 565-571 | nd | 827.4 | | NPDPWAK |
| 572-587 | 1952.09 | 1951.93 | 0.16 | NLNEKDYELLCLDGTR |
| 577-587 | 1353.66 | 1353.62 | 0.03 | DYELLCLDGTR |
| 588-600 | 1585.90 | 1585.77 | 0.13 | KPVEEYANCHLAR |
| 601-609 | 963.60 | 963.52 | 0.08 | APNHAVVTR |
| 610-612 | nd | 390.23 | | KDK |
| 612-621 | 1124.66 | 1124.61 | 0.04 | EACVHKILR |
| 622-642 | nd | 2515.12 | | QQQHLFGSNVTDCSGNFCLFR |
| 643-646 | nd | 464.24 | | SETK |
| 647-659 | 1564.92 | 1564.79 | 0.13 | DLLFRDDTVCLAK |
| 669-676 | 999.56 | 999.49 | 0.06 | YLGEEYVK |
| 683-696 | 1658.85 | 1658.78 | 0.08 | KCSTSSLLEACTFR |
| 684-696 | 1530.79 | 1530.68 | 0.11 | CSTSSLLEACTFR |

(a) Position numbering is for the full length transferrin precursor (the mature protein start at position 20); (b) monoisotopic masses; (c) difference between observed and theoretical mass; (nd) not detected sequences.

TABLE 2

List of possible glycopeptides detected by nanospray FTMS analysis of tryptic digests of sialo and asialotransferrin.

| | Observed (m/z) (charge) | Observed mass | Carbohydrate structure | Peptide sequence | Theoretical mass | Δmass (Da) |
|---|---|---|---|---|---|---|
| Sialo-transferrin | 1434.61 (4+) | 5733.429 (FTMS) 5736 (MALDI) | | CGLVPVLAENYNKSDNCEDTPEAG YFAVAVVK Peptide [421-452] (Asn$^{432}$) | 5733.426 | +0.003 |
| | 1466.38 (4+) | | | CGLVPVLAENYNKSDNCEDTPEAG YFAVAVVKK | | |
| | 1227.24 (3+) | 3680.530 (FTMS) 3683 (MALDI) | | CGLVPVLAENYNK Peptide [421-433] (Asn$^{432}$) | 3680.512 | +0.018 |
| | 1573.97 (3+) 1180.72 (4+) | 4718.887 (FTMS) 4723 (MALDI) | | QQQHLFGSNVTDCSGNFCLFR Peptide [622-642] (Asn$^{630}$) | 4718.889 | −0.001 |

TABLE 2-continued

List of possible glycopeptides detected by nanospray FTMS analysis of tryptic digests of sialo and asialotransferrin.

| | Observed (m/z) (charge) | Observed mass | Carbohydrate structure | Peptide sequence | Theoretical mass | Δmass (Da) |
|---|---|---|---|---|---|---|
| Asialo-transferrin | 1388.23 (3+) | 4161.686 (FTMS) 4163 (MALDI) | | QQQHLFGSNVTDCSGNFCLFR Peptide [622-642] (Asn$^{630}$) | 4161.730 | −0.043 |
| | 1347.08 (2+) | 2691.177 (FTMS) nd (MALDI) | | CGLVPVLAENYNK Peptide [421-433] (Asn$^{432}$) | 2692.163 | +0.014 |

■ N-acetylglucosamine
○ mannose
◇ galactose
★ sialic acid
▲ fucose

FTMS observed masses are monoisotopic. MALDI observed masses are average. Theoretical masses are monoisotopic. Delta mass corresponds to the difference between FTMS observed mass and theoretical mass.
The glycation site is shown in bold in the peptide sequence.

We claim:

1. A method for diagnosing a central nervous system leukodystrophy in patients, comprising the steps of separating asialo- and sialo-transferrin isoforms in a cerebrospinal fluid sample taken from said patient and control subjects who do not have a central nervous system leukodystrophy, identifying said transferrin isoforms, then separately quantifying the separated sialotransferrin and asialotransferrin isoforms, wherein a diminution of asialotransferrin concentration, but not that of sialotransferrin, relative to asialotransferrin concentration in said control subjects, is diagnostic for said leukodystrophy.

2. The method of claim 1, wherein said leukodystrophy is Childhood Onset Ataxia and CNS Hypomyelination (CACH), also known as Vanishing White Matter Disease (VWM).

3. The method of claim 1, wherein said transferrin isoform separation step is carried out by 2-dimensional gel chromatography.

4. The method of claim 3, wherein said separated transferrin isoforms are quantified by staining said isoforms, followed by image analysis of the mass and density of each stained isoform.

5. The method of claim 1, wherein said separated transferrin isoforms are quantified by mass spectrometric techniques.

* * * * *

SEQUENCE LISTING

<160> NUMBER OF SEQ ID NOS: 62

<210> SEQ ID NO 1
<211> LENGTH: 26
<212> TYPE: PRT
<213> ORGANISM: Homo sapiens

<400> SEQUENCE: 1

Met Arg Leu Ala Val Gly Ala Leu Leu Val Cys Ala Val Leu Gly Leu
1               5                   10                  15

Cys Leu Ala Val Pro Asp Lys Thr Val Arg
            20                  25

<210> SEQ ID NO 2
<211> LENGTH: 11
<212> TYPE: PRT
<213> ORGANISM: Homo sapiens

<400> SEQUENCE: 2

Trp Cys Ala Val Ser Glu His Glu Ala Thr Lys
1               5                   10

<210> SEQ ID NO 3
<211> LENGTH: 5
<212> TYPE: PRT
<213> ORGANISM: Homo sapiens

<400> SEQUENCE: 3

Cys Gln Ser Phe Arg
1               5

<210> SEQ ID NO 4
<211> LENGTH: 4
<212> TYPE: PRT
<213> ORGANISM: Homo sapiens

<400> SEQUENCE: 4

Asp His Met Lys
1

<210> SEQ ID NO 5
<211> LENGTH: 14
<212> TYPE: PRT
<213> ORGANISM: Homo sapiens

<400> SEQUENCE: 5

Ser Val Ile Pro Ser Asp Gly Pro Ser Val Ala Cys Val Lys
1               5                   10

<210> SEQ ID NO 6
<211> LENGTH: 8
<212> TYPE: PRT
<213> ORGANISM: Homo sapiens

<400> SEQUENCE: 6

Ala Ser Tyr Leu Asp Cys Ile Arg
1               5

<210> SEQ ID NO 7
<211> LENGTH: 6
<212> TYPE: PRT
<213> ORGANISM: Homo sapiens

```
<400> SEQUENCE: 7

Ala Ile Ala Ala Asn Val
1               5

<210> SEQ ID NO 8
<211> LENGTH: 10
<212> TYPE: PRT
<213> ORGANISM: Homo sapiens

<400> SEQUENCE: 8

Pro Val Val Ala Glu Phe Tyr Gly Ser Lys
1               5                   10

<210> SEQ ID NO 9
<211> LENGTH: 14
<212> TYPE: PRT
<213> ORGANISM: Homo sapiens

<400> SEQUENCE: 9

Glu Asp Pro Gln Thr Phe Tyr Tyr Ala Val Ala Val Val Lys
1               5                   10

<210> SEQ ID NO 10
<211> LENGTH: 11
<212> TYPE: PRT
<213> ORGANISM: Homo sapiens

<400> SEQUENCE: 10

Lys Asp Ser Gly Phe Gln Met Asn Gln Leu Arg
1               5                   10

<210> SEQ ID NO 11
<211> LENGTH: 10
<212> TYPE: PRT
<213> ORGANISM: Homo sapiens

<400> SEQUENCE: 11

Asp Ser Gly Phe Gln Met Asn Gln Leu Arg
1               5                   10

<210> SEQ ID NO 12
<211> LENGTH: 11
<212> TYPE: PRT
<213> ORGANISM: Homo sapiens

<400> SEQUENCE: 12

Gly Lys Lys Ser Cys His Thr Gly Leu Gly Arg
1               5                   10

<210> SEQ ID NO 13
<211> LENGTH: 19
<212> TYPE: PRT
<213> ORGANISM: Homo sapiens

<400> SEQUENCE: 13

Ser Ala Gly Trp Asn Ile Pro Ile Gly Leu Leu Tyr Cys Asp Leu Pro
1               5                   10                  15

Glu Pro Arg

<210> SEQ ID NO 14
<211> LENGTH: 8
<212> TYPE: PRT
<213> ORGANISM: Homo sapiens
```

-continued

```
<400> SEQUENCE: 14

Lys Pro Leu Glu Lys Ala Val Ala
1               5

<210> SEQ ID NO 15
<211> LENGTH: 10
<212> TYPE: PRT
<213> ORGANISM: Homo sapiens

<400> SEQUENCE: 15

Gln Tyr Phe Gly Tyr Ser Gly Ala Phe Lys
1               5                   10

<210> SEQ ID NO 16
<211> LENGTH: 13
<212> TYPE: PRT
<213> ORGANISM: Homo sapiens

<400> SEQUENCE: 16

Cys Leu Lys Asp Gly Ala Gly Asp Val Ala Phe Val Lys
1               5                   10

<210> SEQ ID NO 17
<211> LENGTH: 10
<212> TYPE: PRT
<213> ORGANISM: Homo sapiens

<400> SEQUENCE: 17

Asp Gly Ala Gly Asp Val Ala Phe Val Lys
1               5                   10

<210> SEQ ID NO 18
<211> LENGTH: 11
<212> TYPE: PRT
<213> ORGANISM: Homo sapiens

<400> SEQUENCE: 18

His Ser Thr Ile Phe Glu Asn Leu Ala Asn Lys
1               5                   10

<210> SEQ ID NO 19
<211> LENGTH: 15
<212> TYPE: PRT
<213> ORGANISM: Homo sapiens

<400> SEQUENCE: 19

Ala Asp Arg Asp Gln Tyr Glu Leu Leu Cys Leu Asp Asn Thr Arg
1               5                   10                  15

<210> SEQ ID NO 20
<211> LENGTH: 8
<212> TYPE: PRT
<213> ORGANISM: Homo sapiens

<400> SEQUENCE: 20

Lys Pro Val Asp Glu Tyr Lys Asp
1               5

<210> SEQ ID NO 21
<211> LENGTH: 9
<212> TYPE: PRT
<213> ORGANISM: Homo sapiens

<400> SEQUENCE: 21
```

```
Val Pro Ser His Thr Val Val Ala Arg
1               5
```

<210> SEQ ID NO 22
<211> LENGTH: 15
<212> TYPE: PRT
<213> ORGANISM: Homo sapiens

<400> SEQUENCE: 22

```
Asp Cys His Leu Ala Gln Val Pro Ser His Thr Val Val Ala Arg
1               5                   10                  15
```

<210> SEQ ID NO 23
<211> LENGTH: 7
<212> TYPE: PRT
<213> ORGANISM: Homo sapiens

<400> SEQUENCE: 23

```
Ser Met Gly Gly Lys Glu Asp
1               5
```

<210> SEQ ID NO 24
<211> LENGTH: 10
<212> TYPE: PRT
<213> ORGANISM: Homo sapiens

<400> SEQUENCE: 24

```
Gln Ala Gln Glu His Phe Gly Lys Asp Lys
1               5                   10
```

<210> SEQ ID NO 25
<211> LENGTH: 13
<212> TYPE: PRT
<213> ORGANISM: Homo sapiens

<400> SEQUENCE: 25

```
Ser Lys Glu Phe Gln Leu Phe Ser Ser Pro His Gly Lys
1               5                   10
```

<210> SEQ ID NO 26
<211> LENGTH: 11
<212> TYPE: PRT
<213> ORGANISM: Homo sapiens

<400> SEQUENCE: 26

```
Glu Phe Gln Leu Phe Ser Ser Pro His Gly Lys
1               5                   10
```

<210> SEQ ID NO 27
<211> LENGTH: 5
<212> TYPE: PRT
<213> ORGANISM: Homo sapiens

<400> SEQUENCE: 27

```
Asp Leu Leu Phe Lys
1               5
```

<210> SEQ ID NO 28
<211> LENGTH: 8
<212> TYPE: PRT
<213> ORGANISM: Homo sapiens

<400> SEQUENCE: 28

```
Asp Ser Ala His Gly Phe Leu Lys
1               5
```

<210> SEQ ID NO 29
<211> LENGTH: 12
<212> TYPE: PRT
<213> ORGANISM: Homo sapiens

<400> SEQUENCE: 29

Asp Ser Ala His Gly Phe Leu Lys Val Pro Pro Arg
1               5                   10

<210> SEQ ID NO 30
<211> LENGTH: 4
<212> TYPE: PRT
<213> ORGANISM: Homo sapiens

<400> SEQUENCE: 30

Met Asp Ala Lys
1

<210> SEQ ID NO 31
<211> LENGTH: 12
<212> TYPE: PRT
<213> ORGANISM: Homo sapiens

<400> SEQUENCE: 31

Met Tyr Leu Gly Tyr Glu Tyr Val Thr Ala Ile Arg
1               5                   10

<210> SEQ ID NO 32
<211> LENGTH: 16
<212> TYPE: PRT
<213> ORGANISM: Homo sapiens

<400> SEQUENCE: 32

Glu Gly Thr Cys Pro Glu Ala Pro Thr Asp Glu Cys Lys Pro Val Lys
1               5                   10                  15

<210> SEQ ID NO 33
<211> LENGTH: 9
<212> TYPE: PRT
<213> ORGANISM: Homo sapiens

<400> SEQUENCE: 33

Trp Cys Ala Leu Ser His His Glu Arg
1               5

<210> SEQ ID NO 34
<211> LENGTH: 13
<212> TYPE: PRT
<213> ORGANISM: Homo sapiens

<400> SEQUENCE: 34

Leu Lys Cys Asp Glu Trp Ser Val Asn Ser Val Gly Lys
1               5                   10

<210> SEQ ID NO 35
<211> LENGTH: 11
<212> TYPE: PRT
<213> ORGANISM: Homo sapiens

<400> SEQUENCE: 35

Cys Asp Glu Trp Ser Val Asn Ser Val Gly Lys
1               5                   10

```
<210> SEQ ID NO 36
<211> LENGTH: 15
<212> TYPE: PRT
<213> ORGANISM: Homo sapiens

<400> SEQUENCE: 36

Ile Glu Cys Val Ser Ala Glu Thr Thr Glu Asp Cys Ile Ala Lys
1               5                   10                  15

<210> SEQ ID NO 37
<211> LENGTH: 21
<212> TYPE: PRT
<213> ORGANISM: Homo sapiens

<400> SEQUENCE: 37

Ile Met Asn Gly Glu Ala Asp Ala Met Ser Leu Asp Gly Gly Phe Val
1               5                   10                  15

Tyr Ile Ala Gly Lys
            20

<210> SEQ ID NO 38
<211> LENGTH: 13
<212> TYPE: PRT
<213> ORGANISM: Homo sapiens

<400> SEQUENCE: 38

Cys Gly Leu Val Pro Val Leu Ala Glu Asn Tyr Asn Lys
1               5                   10

<210> SEQ ID NO 39
<211> LENGTH: 19
<212> TYPE: PRT
<213> ORGANISM: Homo sapiens

<400> SEQUENCE: 39

Ser Asp Asn Cys Glu Asp Thr Pro Glu Ala Gly Tyr Phe Ala Val Ala
1               5                   10                  15

Val Val Lys

<210> SEQ ID NO 40
<211> LENGTH: 12
<212> TYPE: PRT
<213> ORGANISM: Homo sapiens

<400> SEQUENCE: 40

Lys Ser Ala Ser Asp Leu Thr Trp Asp Asn Leu Lys
1               5                   10

<210> SEQ ID NO 41
<211> LENGTH: 11
<212> TYPE: PRT
<213> ORGANISM: Homo sapiens

<400> SEQUENCE: 41

Ser Ala Ser Asp Leu Thr Trp Asp Asn Leu Lys
1               5                   10

<210> SEQ ID NO 42
<211> LENGTH: 9
<212> TYPE: PRT
<213> ORGANISM: Homo sapiens

<400> SEQUENCE: 42

Lys Ser Cys His Thr Ala Val Gly Arg
```

```
                                1               5

<210> SEQ ID NO 43
<211> LENGTH: 8
<212> TYPE: PRT
<213> ORGANISM: Homo sapiens

<400> SEQUENCE: 43

Ser Cys His Thr Ala Val Gly Arg
1               5

<210> SEQ ID NO 44
<211> LENGTH: 14
<212> TYPE: PRT
<213> ORGANISM: Homo sapiens

<400> SEQUENCE: 44

Thr Ala Gly Trp Asn Ile Pro Met Gly Leu Leu Tyr Asn Lys
1               5                   10

<210> SEQ ID NO 45
<211> LENGTH: 27
<212> TYPE: PRT
<213> ORGANISM: Homo sapiens

<400> SEQUENCE: 45

Ile Asn His Cys Arg Phe Asp Glu Phe Phe Ser Glu Gly Cys Ala Pro
1               5                   10                  15

Gly Ser Lys Lys Lys Asp Ser Ser Leu Cys Lys
            20                  25

<210> SEQ ID NO 46
<211> LENGTH: 15
<212> TYPE: PRT
<213> ORGANISM: Homo sapiens

<400> SEQUENCE: 46

Leu Cys Met Gly Ser Gly Leu Asn Leu Cys Glu Pro Asn Asn Lys
1               5                   10                  15

<210> SEQ ID NO 47
<211> LENGTH: 11
<212> TYPE: PRT
<213> ORGANISM: Homo sapiens

<400> SEQUENCE: 47

Glu Gly Tyr Tyr Gly Tyr Thr Gly Ala Phe Arg
1               5                   10

<210> SEQ ID NO 48
<211> LENGTH: 12
<212> TYPE: PRT
<213> ORGANISM: Homo sapiens

<400> SEQUENCE: 48

Cys Leu Val Glu Lys Gly Asp Val Ala Phe Val Lys
1               5                   10

<210> SEQ ID NO 49
<211> LENGTH: 11
<212> TYPE: PRT
<213> ORGANISM: Homo sapiens

<400> SEQUENCE: 49
```

His Gln Thr Val Pro Gln Asn Thr Gly Gly Lys
1               5                   10

<210> SEQ ID NO 50
<211> LENGTH: 7
<212> TYPE: PRT
<213> ORGANISM: Homo sapiens

<400> SEQUENCE: 50

Asn Pro Asp Pro Trp Ala Lys
1               5

<210> SEQ ID NO 51
<211> LENGTH: 16
<212> TYPE: PRT
<213> ORGANISM: Homo sapiens

<400> SEQUENCE: 51

Asn Leu Asn Glu Lys Asp Tyr Glu Leu Leu Cys Leu Asp Gly Thr Arg
1               5                   10                  15

<210> SEQ ID NO 52
<211> LENGTH: 11
<212> TYPE: PRT
<213> ORGANISM: Homo sapiens

<400> SEQUENCE: 52

Asp Tyr Glu Leu Leu Cys Leu Asp Gly Thr Arg
1               5                   10

<210> SEQ ID NO 53
<211> LENGTH: 13
<212> TYPE: PRT
<213> ORGANISM: Homo sapiens

<400> SEQUENCE: 53

Lys Pro Val Glu Glu Tyr Ala Asn Cys His Leu Ala Arg
1               5                   10

<210> SEQ ID NO 54
<211> LENGTH: 9
<212> TYPE: PRT
<213> ORGANISM: Homo sapiens

<400> SEQUENCE: 54

Ala Pro Asn His Ala Val Val Thr Arg
1               5

<210> SEQ ID NO 55
<211> LENGTH: 9
<212> TYPE: PRT
<213> ORGANISM: Homo sapiens

<400> SEQUENCE: 55

Glu Ala Cys Val His Lys Ile Leu Arg
1               5

<210> SEQ ID NO 56
<211> LENGTH: 21
<212> TYPE: PRT
<213> ORGANISM: Homo sapiens

<400> SEQUENCE: 56

Gln Gln Gln His Leu Phe Gly Ser Asn Val Thr Asp Cys Ser Gly Asn
1               5                   10                  15

Phe Cys Leu Phe Arg
          20

<210> SEQ ID NO 57
<211> LENGTH: 4
<212> TYPE: PRT
<213> ORGANISM: Homo sapiens

<400> SEQUENCE: 57

Ser Glu Thr Lys
1

<210> SEQ ID NO 58
<211> LENGTH: 13
<212> TYPE: PRT
<213> ORGANISM: Homo sapiens

<400> SEQUENCE: 58

Asp Leu Leu Phe Arg Asp Asp Thr Val Cys Leu Ala Lys
1               5                   10

<210> SEQ ID NO 59
<211> LENGTH: 8
<212> TYPE: PRT
<213> ORGANISM: Homo sapiens

<400> SEQUENCE: 59

Tyr Leu Gly Glu Glu Tyr Val Lys
1               5

<210> SEQ ID NO 60
<211> LENGTH: 14
<212> TYPE: PRT
<213> ORGANISM: Homo sapiens

<400> SEQUENCE: 60

Lys Cys Ser Thr Ser Ser Leu Leu Glu Ala Cys Thr Phe Arg
1               5                   10

<210> SEQ ID NO 61
<211> LENGTH: 13
<212> TYPE: PRT
<213> ORGANISM: Homo sapiens

<400> SEQUENCE: 61

Cys Ser Thr Ser Ser Leu Leu Glu Ala Cys Thr Phe Arg
1               5                   10

<210> SEQ ID NO 62
<211> LENGTH: 32
<212> TYPE: PRT
<213> ORGANISM: Homo sapiens

<400> SEQUENCE: 62

Cys Gly Leu Val Pro Val Leu Ala Glu Asn Tyr Asn Lys Ser Asp Asn
1               5                   10                  15

Cys Glu Asp Thr Pro Glu Ala Gly Tyr Phe Ala Val Ala Val Val Lys
            20                  25                  30